United States Patent [19]
Campbell

[11] Patent Number: 5,938,699
[45] Date of Patent: Aug. 17, 1999

[54] DISTAL RADIAL ULNAR JOINT RECONSTRUCTION SYSTEM

[76] Inventor: G. Stewart Campbell, 120 Marty St., Redlands, Calif. 92373

[21] Appl. No.: 08/844,164

[22] Filed: Apr. 18, 1997

[51] Int. Cl.[6] ........................................................ A61F 2/42
[52] U.S. Cl. ................................................................ 623/21
[58] Field of Search .......................................... 623/21, 61

[56] References Cited

U.S. PATENT DOCUMENTS

| | | | |
|---|---|---|---|
| 4,040,130 | 8/1977 | Laure | 623/21 |
| 4,059,854 | 11/1977 | Laure | 623/21 |
| 4,063,314 | 12/1977 | Loda | 623/21 |
| 4,106,128 | 8/1978 | Greenwald | 623/21 |
| 4,276,660 | 7/1981 | Laure | 623/21 |
| 4,304,011 | 12/1981 | Whelan | 623/21 |
| 4,352,212 | 10/1982 | Greene | 623/21 |
| 5,108,444 | 4/1992 | Branemark . | |
| 5,549,681 | 8/1996 | Segmüller | 623/21 |

FOREIGN PATENT DOCUMENTS

| | | | |
|---|---|---|---|
| 2660856 | 10/1991 | France | 623/21 |
| 1533685 | 12/1989 | U.S.S.R. | 623/21 |
| 2269752 | 2/1994 | United Kingdom | 623/21 |

OTHER PUBLICATIONS

"The Sauvé–Kapandji Procedure for chronic Dislocation of the Distal Radio–Ulnar Joint with Destruction of the Articular Surface"; Nakamura et al.; Journal of Hand Surgery (Brit. vol., 1992); pp. 127–132.

"The Sauvé–Kapandji Procedure"; J. Taleisnik; Clinical Orthopaedics & Related Research, No. 275; Feb. 1992; pp. 110–123.

Primary Examiner—Michael J. Milano
Attorney, Agent, or Firm—Sheldon & Mak

[57] ABSTRACT

A system for reconstructing a patient's distal ulnar joint includes a prosthetic ball joint having elements for implanting, respectively, in a distal ulnar bone fragment and a distal ulnar stump from which the fragment has been separated, a bone screw by which the fragment is fused to the distal radius also serving to anchor the corresponding joint element. Also disclosed is a method for implanting by excising the segment of the ulnar neck, implanting the ball member, fusing the ulnar fragment in fixed relation to the distal radius with the first bone screw extending through the ball member for anchoring same with the fragment, implanting the socket member on the ulnar stump, and snapping the ball member into engagement with the socket member 28.

8 Claims, 1 Drawing Sheet

5,938,699

DISTAL RADIAL ULNAR JOINT RECONSTRUCTION SYSTEM

BACKGROUND

The present invention relates to distal radial ulnar joint (DRUJ) reconstruction in wrists of patients.

One treatment of chronic DRUJ dislocation is known as the Sauvé-Kapandji procedure, as disclosed in "Nouvelle technique de traitement chirurical des luxations récidivantes isolées de l'extrémité infériure de cubitus. (*Journal de Chirurgie*, 47:589–594.) FIG. 1 shows a patient's wrist 10, distal portions of the radius 11 and ulna 12, a segment 13 of the ulnar neck 14 being excised (a proximal ulnar stub or stump 15 and a distal ulnar fragment 16 being formed). Radio-ulnar articular surfaces (not shown) are decorticated down to cancellous bone, and joint fusion is performed using a cancellous bone screw 17 and material 18 of the excised segment 13 between the facing joint portions to maintain the normal radio-ulnar diameter of the wrist. This operation is commonly used to treat post traumatic incongruity or arthritis of the DRUJ.

Although details of the operative procedure have been refined, the most common complication of the Suave-Kapandji procedure is proximal ulnar stub instability with symptomatic "popping" or "clunking" at the ulnar resection site. Also, the instability of the proximal ulnar stump 16 results in reduction of the spacing from the radius 12 (as shown by solid lines in FIG. 1) that is caused by connective tissue between the radius and the ulnar stump 16, and can produce ulnar impingement syndrome in some cases. Such complications have been observed in up to one-third of patients, and may persist, being major disadvantages of the procedure.

U.S. Pat. No. 5,108,444 to Branemark discloses a joint reconstruction system wherein the distal extremity of the ulna is completely removed and replaced with a guide body that is fastened to the radius and a control element that is fastened to the ulnar stump, the element movably engaging a slot that is formed in the guide body. A major disadvantage of this system is loss of ulnar support for the wrist.

Thus there is a need for a system for reconstruction of the DRUJ that overcomes the disadvantages of the prior art.

SUMMARY

The present invention meets this need by providing a system for reconstructing a patient's distal radio-ulnar joint. In one aspect of the invention, a prosthesis for reconstructing a distal radial ulnar joint between a patient's radius and ulna includes a first anchor member for implantation in fixed relation to a distal ulnar fragment and forming a first spherical element; and a second anchor member for implantation in fixed relation to a proximal ulnar stump and forming a second spherical element, the first and second spherical elements being pivotally and rotatably engagable.

The first spherical element can be a convex ball portion, the second spherical element being a concave cavity surface, the ball portion projecting on a neck portion extremity of the first anchor member. The spherical elements can have snap-together engagement. The pivotal engagement can have an angular range of not less than approximately 10 degrees. Preferably, the angular range is approximately 15 degrees.

The first anchor member can include a barrel portion, a first passage being formed through opposite walls thereof for receiving a radio-ulnar bone screw. The second anchor member can include a sleeve portion for fitting onto the proximal ulnar stump. The sleeve portion can have a second passage formed through opposite walls thereof for receiving an ulnar bone screw.

In another aspect of the invention, a method for reconstructing a patient's radial ulnar joint includes the steps of:

(a) providing a prosthesis comprising first and second anchor members having respective pivotally and rotatably engagable first and second spherical elements;

(b) implanting the first anchor member in fixed relation to a distal ulnar fragment of the patient;

(c) implanting the second member in fixed relation to a proximal ulnar stump of the patient; and (d) engaging the first and second spherical elements for supporting the ulnar stump in approximate alignment with the ulnar fragment while permitting pivotal and rotational movement therebetween.

The method can include the further steps of resecting the patient's ulnar shaft for forming the ulnar fragment and the ulnar stump; and fusing the ulnar fragment to the patient's distal radius. The fusing step can include using a bone screw for connecting the ulnar fragment in fixed relation to the distal radius, the step of implanting the first anchor member including inserting the bone screw through a portion of the first anchor member.

DRAWINGS

These and other features, aspects, and advantages of the present invention will become better understood with reference to the following description, appended claims, and accompanying drawings, where:

DESCRIPTION

Figure 1:
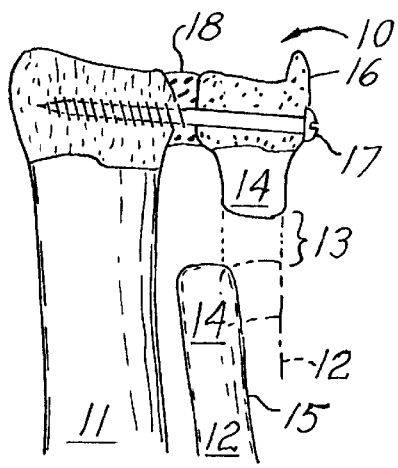
FIG. 1 is a fragmentary lateral sectional view of a patient's wrist region wherein the radial ulnar joint has been reconstructed by a known procedure.
Figure 3:
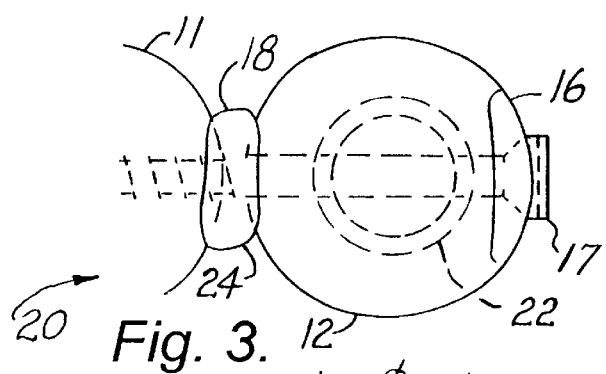
FIG. 3 is a fragmentary longitudinal sectional view of the reconstruction of FIG. 2.
Figure 2:
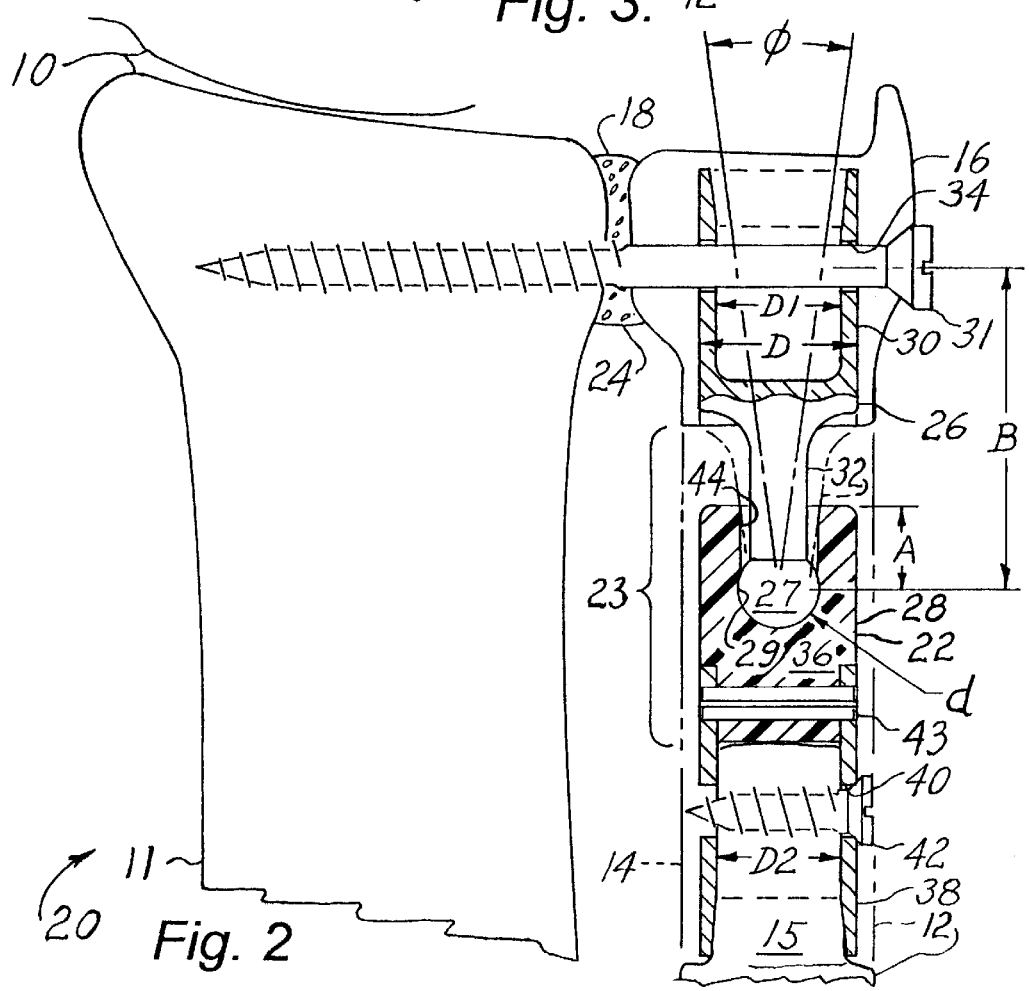
FIG. 2 is a fragmentary sectional view as in FIG. 1, showing an improved joint reconstruction according to the present invention.

The present invention is directed to a system for reconstructing the distal radial ulnar joint (DRUJ) that is particularly effective in maintaining ulnar stability, being suitable in cases of instability of the DRUJ that are in addition cases of arthritis or incongruity. With reference to FIGS. 2 and 3 of the drawings, distal portions of a patient's radius 11 and ulna 12 extend to the wrist 10 as described above in connection with FIG. 1. A reconstruction system 20 of the present invention includes a prosthetic joint unit 22 that is implanted in place of a segment 23 of the ulnar neck 14, the DRUJ itself (designated 24 in FIGS. 2 and 3) being immobilized such as by fusion as described above in connection with FIG. 1, using a counterpart of the cancellous bone screw 17.

The prosthetic joint unit 22 includes a ball member 26 that is implanted in fixed relation to the distal ulnar fragment 16, and a socket member 28 that is fixedly implanted onto an end extremity of the ulnar stump 15, the ball member 26 having a spherical portion 27 that snaps into pivotal and rotational engagement with a spherical cavity surface 29 of the socket member 28. Thus the joint unit 22 retains the ulnar stump 15 in proximal alignment with the fragment 16 while allowing free twisting rotation therebetween, thereby promoting full freedom of wrist movement.

The ball member 26 includes a barrel portion 30 that is adapted for imbedding in the ulnar fragment 16, and a neck portion 32 that locates the spherical portion 27 in spaced relation to the barrel portion 30. The barrel portion 30 has a passage 34 formed through opposite walls thereof for receiving a counterpart of the bone screw, designated first bone screw 31. The barrel portion 30 can be circularly cylindrical, having an outside diameter D and an inside diameter D1, and having a conically tapered end extremity 35 for facilitating insertion into a core-drilled portion of the ulnar fragment 16.

The socket member 28 includes a body portion 36 having the cavity surface 29 formed therein, and a sleeve portion 38 that is adapted for fitting onto the ulnar stump 15, the sleeve portion 38 having a second passage 40 formed therein for receiving a second bone screw 42. The body portion 36 is anchored to the sleeve portion 38 by a roll-pin or other suitable fastener 43. The sleeve portion 38 can be circularly cylindrical, having an inside diameter D2

The cavity surface 29 is centered at a distance A within the body portion 36 from a clearance opening 44 through which the neck portion 32 of the ball member 26 extends, the neck portion 32 thereat being sufficiently smaller for permitting the socket member 28 to pivot through an angle φ relative to the ball member 26 as shown in FIG. 2. This pivotal freedom of movement advantageously reduces bending or twisting loads that would otherwise be imparted to the ulnar fragment 16 and the transplanted bone material 18. As further shown in FIG. 2, the spherical portion 27 of the ball member 26 has a ball diameter d, being spaced a distance B from the first passage 34 (and the first bone screw 17).

The sleeve portion 38 of the socket member 38 can be formed of any suitable bone implantation material, such as 316 stainless steel or titanium, which are also suitable materials for the ball member 26. Suitable materials for the body portion of the socket member 38 include high-density polyethylene. Suitable materials for the base 22 and the spacers 34 include metal and plastic.

Based on the above, the reconstruction system 20 including a method for implanting the prosthetic joint 22 includes the steps of excising the segment 13 of the ulnar neck 14, core-drilling an annular space in the resulting ulnar fragment 16 at the site of the ulnar neck 14 and implanting the ball member 26 with the barrel portion 30 thereof extending into the annular space, fusing the ulnar fragment 16 in spaced relation to the distal radius using the first bone screw 31, the screw 31 extending through the first passage 34 of the barrel portion 30 for anchoring the ball member 26 with the fragment 16, trimming the ulnar stump 15 for fitting into the sleeve portion 38 of the socket member 28, anchoring the socket member 28 to the ulnar stump 15 using the second bone screw extending through the second passage of the sleeve portion 38, and snapping the spherical portion 27 of the ball member 26 into the cavity surface 29 of the socket member 28 for completing the implanted prosthetic joint 22.

An experimental prototype of the prosthetic joint unit 22 has been fabricated as described above, the distance A being approximately 4.5 mm, the distance B being approximately 50 mm, the ball diameter d being approximately 3 mm, the outside diameter D being approximately 8 mm, the diameters D1 and D2 being approximately 5 mm. This prototype of the prosthetic joint unit 22 was tested to compare motion of the ulnar stump 15 following the Sauvé-Kapandji procedure as described above in connection with FIG. 1 with a corresponding procedure that uses the reconstruction system 20 of the present invention.

Two-fresh-frozen cadaver forearms were used. Both forearms were mounted to stabilize the elbow and the hand but to allow free rotation of the forearm and wrist. In one cadaver forearm, a conventional Sauvé-Kapandji procedure was performed through a dorsal ulnar surgical approach. In the second cadaver forearm, the same Sauvé-Kapandji procedure was performed with insertion of the experimental prosthetic joint 22. In both cadaver forearms conventional X-rays were taken and displacement of the ulnar stump 15 measured with respect to the distal ulnar fragment 16 with the forearm in three static positions of rotational alignment: neutral, full pronation and full supination. The following Table shows the displacement of the proximal ulnar stump 16 with respect to the distal ulnar fragment 16, measured from x-rays.

TABLE 1

| Ulnar Stability Comparison | | | |
|---|---|---|---|
| Forearm Position | X-Ray View | SK Only | SK with Prosthesis |
| Neutral | AP | 8 mm | 0 |
|  | LAT | 7 mm | 0 |
| Full Supination | AP | 7 mm | 0 |
| Full Pronation | AP | 13 mm | 0 |

These preliminary results demonstrate that the reconstruction system 20 allows full rotation of the forearm and significantly stabilizes the proximal ulnar stump 15 compared to the control wherein the conventional Sauvé-Kapandji procedure is used.

Although the present invention has been described in considerable detail with reference to certain preferred versions thereof, other versions are possible. For example, the sleeve portion 38 can be formed with axially spaced counterparts of the second passage 40, whereby a pair of the second bone screws may be used for securing to the ulnar stump 15. Therefore, the spirit and scope of the appended claims should not necessarily be limited to the description of the preferred versions contained herein.

What is claimed is:

1. A prosthesis for reconstructing a distal radial ulnar joint between a patient's radius and ulna, the prosthesis comprising:

(a) a first anchor member for implantation in fixed relation to a distal ulnar fragment and forming a first spherical element, the first anchor member including a barrel portion, a first passage being formed through opposite walls thereof for receiving a radio-ulnar bone screw;

(b) a second anchor member for implantation in fixed relation to a proximal ulnar stump and forming a second spherical element, the first and second spherical elements being pivotally and rotatably engagable.

2. The prosthesis of claim 1, wherein the first spherical element is a convex ball portion and the second spherical element is a concave cavity surface, the ball portion projecting on a neck portion extremity of the first anchor member.

3. The prosthesis of claim 1, wherein the spherical elements have snap-together engagement.

4. The prosthesis of claim 1, wherein the pivotal engagement has an angular range of not less than approximately 10 degrees.

5. The prosthesis of claim 4, wherein the angular range is approximately 15 degrees.

6. A prosthesis for reconstructing a distal radial ulnar joint between a patient's radius and ulna, the prosthesis comprising:

(a) a first anchor member for implantation in fixed relation to a distal ulnar fragment and forming a first spherical element;

(b) a second anchor member for implantation in fixed relation to a proximal ulnar stump and forming a second spherical element, the first and second spherical elements being pivotally and rotatably engagable, the second anchor member including a sleeve portion for fitting onto the proximal ulnar stump.

7. The prosthesis of claim 6, wherein the sleeve portion has a second passage formed through opposite walls thereof for receiving an ulnar bone screw.

8. A prosthesis for reconstructing a distal radial ulnar joint between a patient's radius and ulna, the prosthesis comprising:

(a) a first anchor member for implantation in fixed relation to a distal ulnar fragment and having a convex ball portion, a barrel portion, and an interconnecting neck portion, a first passage being formed through opposite walls of the barrel portion for receiving a radio-ulnar bone screw; and (b) a second anchor member for implantation in fixed relation to a proximal ulnar stump and having a concave cavity surface, the second anchor member also including a sleeve portion for fitting onto the ulnar stump, the sleeve portion having a second passage formed through opposite walls thereof for receiving an ulnar bone screw, the ball portion and the cavity surface being pivotally and rotatably engagable, the pivotal engagement having an angular range of not less than approximately 10 degrees.

* * * * *